United States Patent

Griffith et al.

Patent Number: 5,714,500
Date of Patent: Feb. 3, 1998

[54] 2-PHENYL- AND 2-THIENYL-(2)-PIPERIDINE DERIVATIVES HAVING NEUROPROTECTIVE PROPERTIES

[75] Inventors: Ronald Conrad Griffith; Richard Jon Schmiesing, both of Pittsford; Robert John Murray, Rochester, all of N.Y.

[73] Assignee: Astra AB, Södertälju, Sweden

[21] Appl. No.: 39,221

[22] Filed: Mar. 4, 1994

Related U.S. Application Data

[63] Continuation of Ser. No. 597,147, Oct. 15, 1990, abandoned.

[51] Int. Cl.⁶ .................. A61K 31/445; C07D 211/12; C07D 211/14; C07D 409/04
[52] U.S. Cl. .................. 514/317; 514/326; 546/192; 546/213; 546/232; 546/240
[58] Field of Search .................. 546/213, 192, 546/232, 240; 514/326, 317

[56] References Cited

U.S. PATENT DOCUMENTS

| | | | |
|---|---|---|---|
| 2,524,643 | 10/1950 | Walter | 546/216 |
| 2,636,881 | 4/1953 | Schultz | 546/192 |
| 5,109,017 | 4/1992 | Schmiesing | 514/438 |

OTHER PUBLICATIONS

Zezza et al "Reaction of Organolithium Regeants" J. Org. Chem. 49 4397-99 (1984).
Leonard et al "Unsaturated Swines. X." J. Am. Chem. Soc. 79 5279-92 (1957).
Loew et al "Structure Activity Studies of Morphine Fragments" Eur. J. Med. Chem. 26 763-773 (1991).
Morrison & Boyd "Organic Chemistry" Allyn & Baem Co., p. 631, 746 (1973).

*Primary Examiner*—Ceila Chang
*Attorney, Agent, or Firm*—McAulay Fisher Nissen Goldberg & Kiel, LLP

[57] ABSTRACT

Compounds of formula (I)

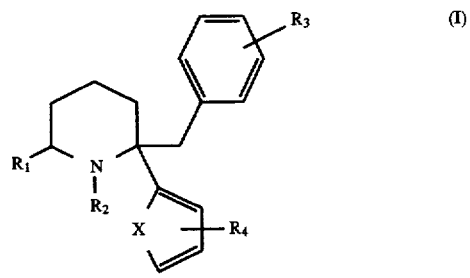

in which $R_1$ is hydrogen, $R_2$ is hydrogen or $C_{1-6}$ alkyl, $R_3$ and $R_4$ independently represent one or more radicals selected from hydrogen, $NH_2$, $NO_2$, halogen, hydroxy, $C_{1-6}$ alkoxy or $C_{1-6}$ alkyl, X represents S or —CH=CH— group and pharmaceutically acceptable salts are NMDA receptor antagonists.

9 Claims, No Drawings

2-PHENYL- AND 2-THIENYL-(2)-PIPERIDINE DERIVATIVES HAVING NEUROPROTECTIVE PROPERTIES

This application is a 371 of PCT/US91/07522 filed Oct. 11, 1991 which is a continuation of U.S. application Ser. No. 07/597,147 filed Oct. 15, 1990, now abandoned.

This invention relates to novel piperidine derivatives, processes for the preparation, pharmaceutical formulations containing them and their neuroprotective properties.

BACKGROUND

Compounds which possess N-methyl-(d)-aspartate (NMDA) blocking properties are useful in the treatment and/or prevention of neurological disorders such as stroke, cerebral ischaemia, cerebral palsy, hypoglycaemia, epilepsy, Alzheimer's disease, Huntington's chorea, Olivo-ponto-cerebellar atrophy, perinatal asphyxia and anoxia.

Zezza et al. described the synthesis of 2,2-diphenyl-pyrrolidines, piperidines and 3,4,5,6-tetrahydro-1H-azepines[J. Org. Chem. 49, 4397–4399(1984)].

DETAILED DESCRIPTION

According to the invention, we provide compounds of the formula I

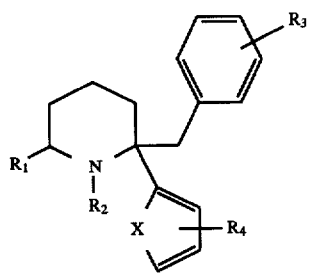

in which:

$R_1$ and $R_2$ which may be the same or different, represent hydrogen or $C_{1-6}$ alkyl, $R_3$ and $R_4$ independently represent one or more radicals selected from hydrogen, $NH_2$, $NO_2$, halogen, hydroxyl, $C_{1-6}$ alkoxy or $C_{1-6}$ alkyl, X represents S or a —CH=CH— group, and pharmaceutically acceptable derivatives thereof.

Pharmaceutically acceptable derivatives include acid addition salts and bioprecursors (prodrugs) of the compound of formula I Pharmaceutically acceptable acid addition salts of the compounds of formula I include salts of mineral acids, for example, hydrohalic acids, e.g. hydrochloric or hydrobromic; or organic acids, for example, formic, acetic or lactic acids. The acid may be polybasic, for example, sulphuric, fumaric, maleic or citric acid.

Suitable bioprecursors of the compounds of formula I include $C_{1-6}$ alkanoyl amides, urethane derivatives and amino acid amide derivatives of one or more of the amino groups, and when a compound of formula I bears a hydroxyl group, esters of alkanoic and amino acids. Urethane derivatives include $C_{1-5}$ alkoxycarbonyl groups. Amino acid amide derivatives may be formed from alpha-amino acids.

Alpha-amino acids may be represented by the formula II,

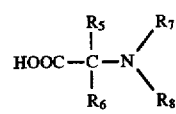

in which, $R_5$ represents hydrogen, $C_{1-6}$ alkyl, hydroxy- $C_{1-2}$ alkyl, mercaptomethyl, (methylthio)$C_{1-2}$ alkyl, carboxy-$C_{1-2}$ alkyl, 2-($C_{1-3}$ alkoxy)ethyl, (aminocarbonyl)$C_{1-2}$ alkyl, amino-$C_{1-4}$ alkyl, 3-imidazolylmethyl, phenylmethyl or (4-hydroxyphenyl)-methyl, or in addition, $R_5$ together with the adjacent nitrogen may represent a piperidine, pyrrolidine or a 2-pyrrolidinone ring; and $R_6$, $R_7$ and $R_8$ independently represent hydrogen or $C_{1-6}$ alkyl, or in addition, $R_7$ and $R_8$ taken together with the nitrogen to which they are attached may represent a $C_{4-5}$ N heterocyclic ring;

Certain compounds of formulas I and II may exist in different stereoisomeric forms, including optical enantiomeric forms. All are included within the scope of the invention.

According to another aspect of the invention, there is provided a process for the preparation of the compounds of formula I or pharmaceutically acceptable salts thereof, which comprises (a) preparing a compound of formula I in which $R_1$ is hydrogen by reducing the corresponding compound of the formula III

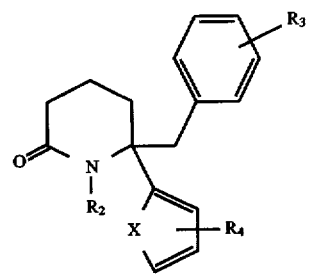

in which $R_2$, $R_3$, $R_4$ and X are as defined above, or (b) preparing a compound of formula I in which $R_2$ is $C_{1-6}$ alkyl by reacting the corresponding compound of formula I in which $R_2$ is hydrogen with an alkylating agent of the formula, $C_{1-6}$ alkyl-Y in which Y is a suitable leaving group, or (c) preparing a compound of formula I in which $R_2$ is $C_{1-6}$ alkyl by reducing the corresponding compound of formula I in which $R_2$ represents a $C_{1-6}$ alkanoyl group or a urethane group, or (d) preparing a compound of formula I by reducing the corresponding compound of formula IV,

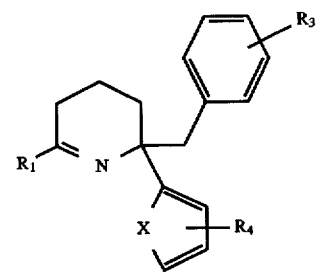

in which $R_1$, $R_3$, $R_4$ and X are as defined above, or (e) producing a compound of formula I containing one or more amino or hydroxy groups by removing a protecting group from a compound of formula I in which one or more of the amino or hydroxy groups is protected;

and where desired or necesssary converting the resulting compound of formula I into a pharmaceutically acceptable derivative thereof or vice-versa.

The reduction reaction of process (a) may be carried out with a hydride reducing agent, for example, diborane or sodium bis(2-methoxyethoxy)-aluminum hydride in an aprotic solvent, for example, tetrahydrofuran. The reduction may be carried out at a temperature of, for example, from 0°–100° C.

The alkylation reaction of process (b) may be carried out with an alkylating reagent, for example, iodomethane, bromoethane or methyl p-toluenesulfonate, in the presence of a base, for example, sodium hydroxide or pyridine in a suitable solvent, for example, water, ethanol or tetrahydrofuran or mixtures of the solvents, and at a temperature of, for example, from 0°–100° C.

The reduction reaction of process (c) may be carried out with a hydride reducing agent, for example, diborane or sodium bis(2-methoxyethoxy)-aluminum hydride in an aprotic solvent, for example, tetrahydrofuran. The reduction may be carried out at a temperature of, for example, from 0°–100° C.

The reduction of process (d) may be carried out with a nucleophilic reducing agent, for example, a complex metal hydride such as sodium (2-methoxyethoxy) aluminum hydride, lithium aluminum hydride, sodium borohydride or sodium cyanoborohydride. The reduction may be carried out in a suitable solvent. Aprotic solvents, for example, tetrahydrofuran are preferred for the aluminum hydrides while protic solvents, for example, methanol or ethanol are preferred for the boron hydrides. The reaction with the nitrogen nucleophile and the reduction reactions may be carried out at a temperature of, for example, from. 0°–100° C.

In the reaction of process (e), removal of the protecting group depends on the nature of the protecting group and includes acidic or basic cleavage or hydrogenolysis. Suitable amine protecting groups are, for example, ethoxycarbonyl, benzyloxycarbonyl, t-butyloxycarbonyl or $C_{1-3}$ alkanoyl. Further protecting groups and methods for their removal are described in T. W. Greene, Protective Groups in Organic Synthesis, Wiley-Interscience, 1981.

Acid addition salts may be formed by reacting the free base, or a salt or derivative thereof with one or more equivalents of the appropriate acid. The reaction may be carried out in a solvent in which the salt is insoluble or in which the salt is soluble or in mixtures of the solvents. Acid addition salts may be converted to the corresponding base, for example, by reacting the salt with sodium hydroxide in water at room temperature. Suitable bioprecursor forms of a compound of the formula I may be prepared by reacting the corresponding compound of formula I in which one or more of the amino groups is unprotected with a $C_{1-6}$ alkanoic acid anhydride, $C_{1-6}$ alkanoyl halide, $C_{1-6}$ haloformate ester, or an amino acid or a carboxyl activated derivative thereof. Conventional acylation techniques for amines may be used by reacting with acid halides, acid anhydrides or haloformate esters, for example, acetic anhydride, acetyl chloride or ethyl chloroformate. The reactions may be carried out in the absence of a solvent; however, a suitable inert solvent may be used, for example, toluene, methylene chloride or tetrahydrofuran. The reactions may be carried out at a temperature of, for example, from 0°–100° C. The condensation with alpha-amino acid derivatives may be carried out in conditions similar to those used for the synthesis of peptide bonds in protein chemistry, e.g. by carrying out the reaction in the presence of N,N'-carbonyldiimidazole in a polar aprotic solvent or using a hindered base, e.g. triethylamine and an alkyl chloroformate. When one or both of the amino acid nitrogen substituents is hydrogen the nitrogen atom requires protection. One particularly suitable protecting group is benzyloxycarbonyl, which may readily be removed by hydrogenolysis or hydrogen bromide in acetic acid. Other groups that may be mentioned include t-butyloxycarbonyl, (Boc), which is removed by standing the peptide in cold trifluoroacetic acid; Fmoc, which may be removed by treatment with dilute piperidine (20% in DMF); (4-methoxybenzyl)oxy-carbonyl and 2-nitrophenylsulphenyl. Further protecting groups and methods for their removal are described in T. W. Greene, Protective Groups in Organic Synthesis, Wiley-Interscience, 1981.

The starting materials for the products of reaction (a) can be made by a variety of methods, for example;

compounds of formula III in which $R_2$ is hydrogen may be prepared by:

1) reacting the corresponding compound of formula V

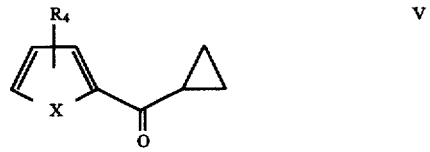

in which $R_4$ and X are as defined above, with a corresponding Grignard reagent of formula VI

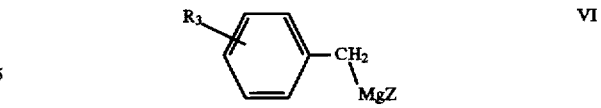

in which $R_3$ is as defined above and Z represents a halogen, to give the corresponding compound of formula VII

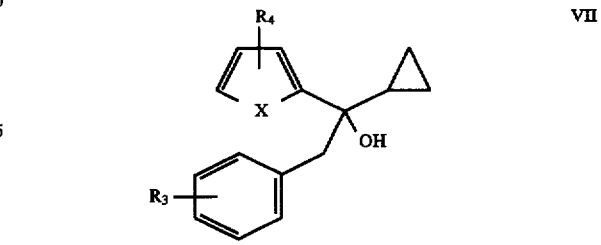

2) reacting a compound of formula VII with a hydrogen halide, for example, hydrobromic acid to give the corresponding compound of formula VIII

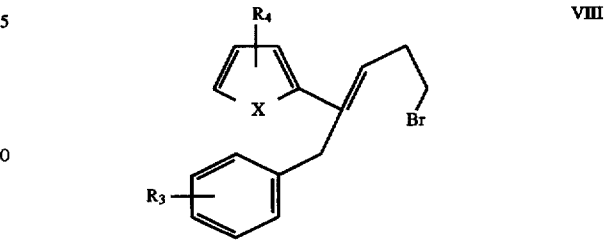

3) reacting a compound of formula VIII with an alkali cyanide, for example, sodium cyanide, followed by hydrolysis to give the corresponding compound of the formula IX

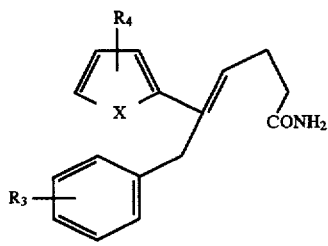

4) cyclization of a compound of formula IX to the corresponding compound of the formula III.

The Grignard reaction of step 1 is carried out by conventional methods, for example, in diethyl ether at a temperature of, for example, from 0°–30° C. The bromination reaction may be carried out with, for example, 48% HBr (aqueous) in the presence of an inert solvent, for example, toluene at room temperature. Replacement of the bromine with cyanide is carried out with sodium cyanide in a polar solvent, for example, dimethylsulfoxide at a temperature of, for example, 30°–100° C. The nitrile can be hydrolyzed with aqueous alkali, for example, aqueous NaOH preferably under peroxide catalyzed phase transfer conditions, for example, in the presence of tetrabutylammonium hydrogen sulfate and hydrogen peroxide, and an inert solvent, for example, methylene chloride. Cyclization of the amide may be carried out under dehydrating conditions with strong acid, for example, with phosphorous pentoxide and methanesulfonic acid at a temperature of, for example, from 20°–120° C.

The starting materials for the products of reaction (d) can be made by a variety of methods, for example, by cyclization of a corresponding compound of formula X

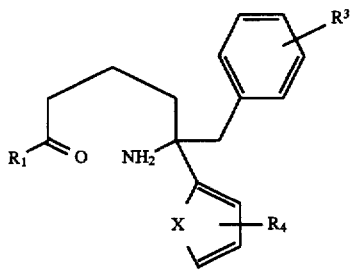

in which $R_1$, $R_3$ and $R_4$ are as defined above.

The cyclization reaction may be carried out under dehydrating conditions, for example, with acid catalysts, for example p-toluenesulfonic acid, in an inert solvent, for example, toluene, and at a temperature of, for example, from 20°–120° C.

Compounds of formulas V, VI, IX and X are either well known or can be prepared from compounds known per se by conventional methods or by modifications thereof as described in the examples.

In the compound of formula I;

alkyl groups which $R_1$, $R_2$, $R_3$ and $R_4$ may represent include methyl, ethyl, propyl, isopropyl, n-butyl, iso-butyl and s-butyl;

alkoxy groups which $R_3$ and $R_4$ may represent include methoxy, ethoxy and propoxy;

halogen groups which $R_3$ and $R_4$ may represent include fluorine, chlorine, bromine or iodine;

We prefer compounds of formula I or a pharmaceutically acceptable derivative thereof, in which;

$R_1$ represents hydrogen, methyl or ethyl, especially hydrogen or methyl;

$R_2$ represents hydrogen, methyl or ethyl, especially hydrogen or methyl;

$R_3$ represents hydrogen, hydroxy, amino or chloro;

$R_4$ represents hydrogen or $C_{1-6}$ alkyl;

We especially prefer compounds in which $R_3$ represents hydrogen.

We especially prefer compounds in which $R_4$ represents hydrogen or methyl.

We especially prefer compounds in which X is a —CH═CH— group.

A subgroup of compounds which are preferred are those in which, $R_1$ is hydrogen or methyl, and $R_2$ is hydrogen.

We prefer prodrugs of the compounds of formula I in which $R_2$ is hydrogen, especially those in which the piperidine nitrogen is substituted with a suitable bioprecursor group.

Suitable bioprecursor groups which may be mentioned include acetyl, propionyl, butanoyl, methoxycarbonyl, ethoxycarbonyl and alpha-amino acids, for example, glycine, alanine, leucine, proline, methionine, serine and sarcosine. Derivatives of alpha-amino acids are preferred, especially glycine.

According to yet another aspect of the invention there is provided the use of a compound of formula I, as defined above, or pharmaceutically acceptable derivatives thereof, in the manufacture of a medicament for use in the prevention and/or treatment of neurological disorders.

Certain compounds of formula I and their pharmaceutically acceptable derivatives are useful because they possess pharmacological activity in animals. The compounds have useful neuroprotective properties. In particular, they possess NMDA blocking properties. Neurodegeneration is known to be caused or accelerated by certain excitatory amino acids found naturally in the central nervous system (CNS). Glutamate is an endogenous amino acid which has been characterized as a fast excitatory transmitter in the mammalian brain. Glutamate is also known as a powerful neurotoxin capable of killing CNS neurons under certain pathologic conditions which accompany stroke and cardiac arrest. It has been shown that the sensitivity of central neurons to hypoxia and ischemia can be reduced by the specific antagonism of post synaptic glutamate receptors. Glutamate is characterized as a broad spectrum agonist having activity at four neuronal excitatory amino acid receptor sites. These receptor sites are named after the amino acids which selectively excite them: kainate (KA), N-methyl-D-aspartate (NMDA), 2-amino-4-phosphonobutyrate(APB) and quisqualate (QUIS). Glutamate is believed to be a mixed agonist capable of binding to and exciting all four receptor types. Thus agents which selectively block or antagonise the action of glutamate at these receptors can prevent neurotoxic injury associated with anoxia, hypoxia or ischemia. In particular, compounds which bind to the NMDA receptor site and selectively block the action of glutamate are useful in the prevention and treatment of neurodegenerative diseases.

In addition, certain compounds of formula I demonstrate anticonvulsant activity by their ability to inhibit maximal electroshock (MES) induced seizures in mice; certain compounds inhibit the onset of convulsions and death induced by administration of NMDA to mice; and certain compounds demonstrate antihypoxia activity by their ability to increase the survival time of mice in an oxygen depleted environment.

Antiepileptic activity may be measured by assessing a compound's ability to prevent the hind limb tonic extension component of the seizure in groups of mice induced by maximal electroshock (MES) after oral or intraperitoneal administration according to the procedures of the Epilepsy Branch, NINCDS as published by R. J. Porter, et al., *Cleve. Clin. Quarterly* 1984, 51, 293, and compared to the standard agents dilantin and phenobarbital. Activities ($ED_{50}$'s) in the range of 10–400 m/k after oral administration in this assay system were obtained.

Certain compounds of this invention may possess useful antihypoxia activity. This activity may be conveniently measured in mice. Groups of mice are tested at various times after the intraperitoneal administration of graded doses of the test compound. The animals' survival time in a temperature controlled hypoxic environment (96% nitrogen and 4% oxygen) is recorded. A statistical comparison is made between coincident vehicle treated animals and the experimental group. The dose-response and minimum active dose (MAD) for compounds are obtained. Other modes of administration can also be used.

NMDA activity may be measured in several ways:

a) NMDA blocking activity is measured by assessing a compound's ability to protect mice from convulsions induced by intravenous administration of 150 m/k of NMDA according to the procedures of Czuczwar et al., (Neurotransmitters, Seizures and Epilepsy III, edited by G. Nistico et al., Raven Press, New York 1986, pages 235–246). Groups of mice are pretreated by 30 min with the test compound by the oral or intraperitoneal routes and then given NMDA. Animals were observed for convulsions as defined by loss of righting reflex and appearance of tonic/clonic seizures. Animals are kept for 60 min after NMDA dosing and mortality was recorded.

b) NMDA receptor antagonist activity is measured in vitro by assaying a compounds ability to inhibit binding of the receptor antagonist 10,11-dihydro-5-methyl-5H-dibenzo[a,d]-cyclohepten-5,10-imine(MK801) to the receptor. The method is described by Foster and Wong, *Br. J. Pharmacol.* 91, 403–409 (1987).

c) NMDA and glycine receptor affinity may also be tested in the [$^3$H]L-glutamate and [$^3$H]glycine binding assays following the method of Monaghan & Cotman, *PNAS*, 83, 7532, (1986) and Watson et al, *Neurosci. Res. Comm.*, 2, 169, (1988).

Certain compounds may act as neuromodulators by interfering with neurotransmitter uptake. Undesirable psychotomimetic effects may be associated with a compounds ability to inhibit dopamine uptake. Inhibition of dopamine uptake may be measured according to the method of Holtz et al, *Molecular Pharmacol.*, 10, 746 (1974).

For the above-mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral or parenteral administration.

According to the invention, there is also provided a pharmaceutical composition comprising preferably less than 80% and more preferably less than 50% by weight of a compound of formula I, or a pharmaceutically acceptable salt thereof, in admixture with a pharmaceutically acceptable adjuvant, diluent or carrier.

Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

Sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, have a broader range of activity, are more potent, produce fewer side effects, are more easily absorbed or have other useful pharmacological properties, compared to known compounds previously used in the therapeutic areas mentioned above. The invention is illustrated, but in no way limited, by the following examples.

EXAMPLE 1

Preparation of 2-phenyl-2-(phenylmethyl)piperidine hydrochloride a) α-Cyclopropyl-α-phenylbenzeneethanol Cyclopropyl phenyl ketone (25 g, 0.171 mol) in diethyl ether (100 mL) was added dropwise to an ice-cooled solution of benzyl magnesium bromide (175 mL of a 1M solution) in ether and the resulting mixture was allowed to warm to room temperature over 2 hours. The reaction was quenched by saturated aqueous $NH_4Cl$. The ether layer was separated and concentrated to give the product alcohol as an oil (40 g).

b) 4,5-Diphenyl-3-pentenyl bromide

The alcohol (40 g, 0.17 mol) from step (a) in toluene (200 mL) was mixed with 48% HBr aqueous and stirred vigorously for 2 hours at room temperature. The toluene layer was separated, washed with water and dried ($MgSO_4$). Concentration to dryness afforded the bromide as a pale yellow oil (45 g).

c) 5,6-Diphenyl-4-hexenenitrile

The bromide (50 g, 0.17 mol) from step (b) was added dropwise to a vigorously stirred mixture of sodium cyanide (11 g) in DMSO (60 mL) at 60° C. The reaction mixture was stirred at 60°–70° C. for 2 hours, cooled and partitioned between ether and water. The ether extract was isolated and concentrated to give the crude nitrile which was purified by chromatography on silica gel and elution with 10%; then 25% ethyl acetate-hexane to give the nitrile as a syrup (24 g).

d) 5,6-Diphenyl-4-hexenamide 5,6-Diphenyl-4-hexenenitrile (36 g) was dissolved in methylene chloride (180 mL) at 0° C. and stirred vigorously while 50% $H_2O_2$ (100 mL), tetrabutyl ammonium hydrogen sulfate (13 g) and 20% NaOH (100 mL) were added successively. The resulting mixture was stirred at 0° C. for 30 minutes, then for 2 hours without cooling. The reaction mixture was poured into $CH_2Cl_2$ and water and the organic layer was separated, washed with water and brine and dried ($MgSO_4$). Concentration of the solvent afforded the crude amide which was purified by silica gel chromatography and elution with 50% ethyl acetate: hexane, then ethyl acetate to give the amide as a solid (30 g).

e) 6-Phenyl-6-(phenylmethyl)-2-piperidinone 5,6-Diphenyl-4-hexenamide (30 g) from step (d) was added to a stirred solution of phosphorous pentoxide (25 g) in methanesulfonic acid (250 mL) at 100°–110° C. The reaction was stirred for several minutes; then the reaction mixture was poured slowly into an ice-cooled mixture of saturated aqueous sodium bicarbonate and ethyl acetate. The mixture was extracted with ethyl acetate and the ethyl acetate layer was separated, washed with aq. $NaHCO_3$, water and brine and dried ($MgSO_4$). Concentration of the solvent to dryness afforded the crude amide which was purified by chromatography on silica gel and elution with 75% ethyl acetate: hexane to give the title compound as a solid (16.5 g).

f) 2-Phenyl-2-(phenylmethyl)piperidine hydrochloride

A solution of 6-Phenyl-6-(phenylmethyl)-2-piperidinone (4 g, 0.015 mol) in THF (150 mL) was added dropwise to 150 mL of $1M.BH_3$ in THF at 0° C. The reaction was refluxed overnight, cooled to 0° C. and decomposed by the addition of 1N.HCL (210 mL). The resulting mixture was heated to reflux for 2 hours then cooled to 0° C., diluted with ethyl acetate and basified with aq. NaOH. The organic layer was separated, washed with water, brine and dried. Concentration of the ethyl acetate afforded the crude amine which was purified by chromatography on silica gel and elution with 75% ethyl acetate-hexane, then ethyl acetate to give the amine as an oil (3.2 g). The amine was treated with hydrogen chloride in isopropanol and diethyl ether was added to precipitate the salt (2.5 g) of the title compound, mp 227°–230° C.

EXAMPLE 2

Resolution of 2-phenyl-2-(phenylmethyl)piperidine

Racemic 2-phenyl-2-(phenylmethyl)piperidine (37.93 g) and di-p-toluoyl-L-tartaric acid (23.6 g) were each dissolved in 87 mL of hot acetone and combined. The solution was refluxed for 15 minutes while the precipitate formed. The warm mixture was filtered and the solids were washed with acetone (150 mL) to give 27.9 g of a diastereoisomeric salt with chiral purity of 95.5%. The solid was slurried with 180 mL of acetone at reflux for 30 minutes, cooled and filtered to give 26.8 g of solid. The solid was then recrystallized from 95% EtOH (300 mL) to give 22.1 g of solid with chiral purity of 100%. $[\alpha]_D=-109.7°$ (C=1.18,MeOH; 22° C.) and mp=154.5°–155.5° C. The salt was converted to the base by slurrying with water (150 mL), conc. $NH_4OH$ (20 mL) and $CH_2Cl_2$ (70 mL). The organic layer was separated, dried ($MgSO_4$) and concentrated to yield 8.22 g of (+)-2-phenyl-2-(phenylmethyl)piperidine as an oil, $[\alpha]_D=+4.15°$ (C=0.987, MeOH; 22° C.).

The filtrates from the diastereoisomeric salt formation were combined and concentrated. The residual solids were slurried with water, conc. $NH_4OH$ and $CH_2Cl_2$ until solution was obtained. The organic layer was separated, dried ($MgSO_4$) and concentrated to give the base (13.3 g) as an oil. The base (13.3 g) was dissolved in hot acetone (90 mL) and a solution of di-p-toluoyl-D-tartaric acid (21.44 g) in hot acetone (100 mL) was added. The solution was refluxed for 15 minutes and then the precipitated solids were filtered from the hot solvent. The solids were reslurried with hot acetone (100 mL) for 30 minutes and filtered to give 29.0 g of the diastereoisomeric salt with optical purity of 95%. The salt (29.0 g) was recrystallized from 95% EtOH (400 mL) to give 23.4 g of the salt with chiral purity of 100%, $[\alpha]_D=+110.11°$ (C=0.979, MeOH; 22° C.) and mp=154.5°–155.5° C. The salt was converted to the base essentially according to the method described above and (−)-2-phenyl-2-(phenylmethyl)piperidine was obtained as an oil (9.22 g), $[\alpha]_D=-3.91°$ (C=1.355, MeOH; 22° C.).

The (+) enantiomer of the base (8.0 g) was dissolved in ether (40 mL) and isopropanol (2 mL) then acidified with dry HCl. A precipitate formed and after 30 minutes additional ether (60 mL) was added and the mixture was warmed gently for 5 minutes. The cooled mixture was filtered to give (−)-2-phenyl-2-(phenylmethyl)piperidine hydrochloride (7.93 g), mp 177.5°–178.5° C., $[\alpha]_D=-48.34°$ (C=0.987, MeOH; 22° C.).

The (−) enantiomer of the base (9.0 g) was converted to the hydrochloride salt by essentially the same procedure as described above to give (+)-2-phenyl-2-(phenylmethyl)piperidine hydrochloride (8.72 g), mp=177.5°–178.5° C., $[\alpha]_D=+48.29°$ (C=0.988, MeOH; 22° C.).

EXAMPLE 3

The compound of Example 1 was tested for aniconvulsant activity against MES induced convulsions and found to have an $ED_{50}$ (po)=25 mg/kg.

What we claim is:

1. A compound of the formula I,

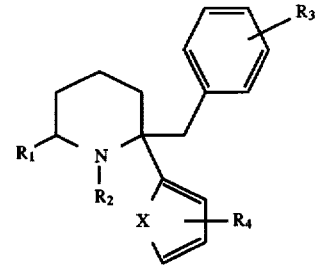

in which:

$R_1$ is hydrogen and $R_2$ represents hydrogen or $C_{1-6}$ alkyl, $R_3$ and $R_4$ independently represent one or more radicals selected from hydrogen, $NH_2$, $NO_2$, halogen, hydroxyl, $C_{1-6}$ alkoxy or $C_{1-6}$ alkyl, X represents S or a —CH=CH— group, and pharmaceutically acceptable derivatives thereof.

2. A compound according to claim 1 in which $R_2$ is hydrogen, methyl or ethyl.

3. A compound according to claim 1 in which $R_3$ is selected from hydrogen, $NH_2$ or chloro.

4. A compound according to claim 1 in which $R_4$ is selected from hydrogen or $C_{1-6}$ alkyl.

5. A compound according to claim 1 in which X is a —CH=CH— group.

6. A compound according to claim 1 which is 2-phenyl-2-(phenylmethyl)piperidine, (−)-2-phenyl-2-(phenylmethyl)piperidine, (+)-2-phenyl-2-(phenylmethyl)piperidine, or a pharmaceutically acceptable salt thereof.

7. A pharmaceutical composition comprising a compound of formula I, as defined in claim 1, or a pharmaceutically acceptable derivative thereof, in association with a pharmaceutically acceptable adjuvant, diluent or carrier.

8. A method for blocking excitatory amino acid action in stroke, cerebral ischaemia, cerebral palsy, hypoglycaemia, epilepsy, Alzheimer's disease, Huntington's chorea, Olivoponto-cerebellar atropy, perinatal asphyxia and anoxia comprising administering to a patient an MNDA receptor antagonistic effective amount of the compound of claim 1.

9. A process for the preparation of the compounds of formula 1, as defined in claim 1, or pharmaceutically acceptable derivatives thereof, which comprises (a) preparing a compound of formula I in which $R_1$ is hydrogen by reducing the corresponding compound of the formula III,

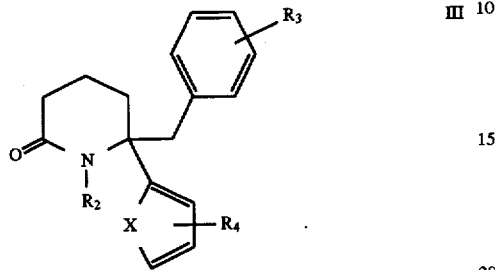

in which $R_2$, $R_3$, $R_4$ and X are as defined above, or (b) preparing a compound of formula I in which $R_2$ is $C_{1-6}$ alkyl by reacting the corresponding compound of formula I in which $R_2$ is hydrogen with an alkylating agent of the formula, $C_{1-6}$ alkyl-Y in which Y is a suitable leaving group, or (c) preparing a compound of formula I in which $R_2$ is $C_{1-6}$ alkyl by reducing the corresponding compound of formula I in which $R_2$ represents a $C_{1-6}$ alkanoyl group or a urethane group, or (d) preparing a compound of formula I by reducing the corresponding compound of formula IV,

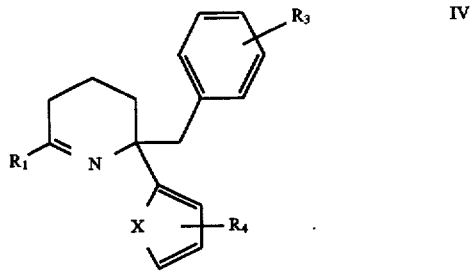

in which $R_1$, $R_3$, $R_4$ and X are as defined above; or (e) producing a compound of formula I containing one or more amino or hydroxy groups by removing a protecting group from a compound of formula I in which one or more of the amino or hydroxy groups is protected;

and where desired or necessary converting the resulting compound of formula I into a pharmaceutically acceptable derivative thereof or vice-versa.

* * * * *